(12) United States Patent
Wu et al.

(10) Patent No.: US 11,065,471 B2
(45) Date of Patent: Jul. 20, 2021

(54) SYSTEMS AND METHODS FOR AUTOMATIC, CUSTOMIZED RADIATION TREATMENT PLAN GENERATION FOR CANCER

(71) Applicants: Duke University, Durham, NC (US); The University of North Carolina at Charlotte, Charlotte, NC (US)

(72) Inventors: Qingrong Jackie Wu, Durham, NC (US); Yaorong Ge, Matthews, NC (US); Taoran Li, Durham, NC (US); Fang-Fang Yin, Durham, NC (US); Yang Sheng, Durham, NC (US)

(73) Assignees: Duke University, Durham, NC (US); The University of North Carolina at Charlotte, Charlotte, NC (US)

( * ) Notice: Subject to any disclaimer, the term of this patent is extended or adjusted under 35 U.S.C. 154(b) by 225 days.

(21) Appl. No.: 15/776,145

(22) PCT Filed: Nov. 21, 2016

(86) PCT No.: PCT/US2016/063204
§ 371 (c)(1),
(2) Date: May 15, 2018

(87) PCT Pub. No.: WO2017/087985
PCT Pub. Date: May 26, 2017

(65) Prior Publication Data
US 2020/0254275 A1    Aug. 13, 2020

Related U.S. Application Data

(60) Provisional application No. 62/267,340, filed on Dec. 15, 2015, provisional application No. 62/257,911, filed on Nov. 20, 2015.

(51) Int. Cl.
*A61N 5/00* (2006.01)
*A61N 5/10* (2006.01)
*G16H 20/40* (2018.01)

(52) U.S. Cl.
CPC ............. *A61N 5/103* (2013.01); *G16H 20/40* (2018.01); *A61N 2005/1041* (2013.01); *A61N 2005/1062* (2013.01)

(58) Field of Classification Search
CPC .... A61N 2005/1041; A61N 2005/1062; A61N 25/103
See application file for complete search history.

(56) References Cited

U.S. PATENT DOCUMENTS 6,327,490 B1    12/2001  Spetz
2002/0080915 A1  6/2002  Frohlich
(Continued)

FOREIGN PATENT DOCUMENTS

EP    3384959 A1    10/2018
WO    03011390 A3    2/2003

OTHER PUBLICATIONS

International Preliminary Report on Patentability and Written Opinion issued in PCT Application No. PCT/US2016/063204 dated May 22, 2018 (six (6) pages).
(Continued)

*Primary Examiner* — Dani Fox
(74) *Attorney, Agent, or Firm* — Olive Law Group, PLLC (57) ABSTRACT

Systems and methods for automatic, customized radiation treatment plan generation for cancer are disclosed. According to an aspect, a method includes receiving data indicating anatomy information of a patient and radiation beam characteristics of a radiation therapy system. Further, the method includes determining energy levels for application of radiation beams to the patient.

27 Claims, 6 Drawing Sheets

(56) References Cited

U.S. PATENT DOCUMENTS

| | | | | |
|---|---|---|---|---|
| 2006/0291621 | A1* | 12/2006 | Yan | A61B 5/0816 |
| | | | | 378/65 |
| 2012/0014507 | A1* | 1/2012 | Wu | A61N 5/10 |
| | | | | 378/65 |
| 2012/0190912 | A1 | 7/2012 | McKenna et al. | |
| 2013/0090549 | A1 | 4/2013 | Meltsner et al. | |
| 2013/0289332 | A1* | 10/2013 | Purdie | A61N 5/1039 |
| | | | | 600/1 |
| 2015/0087879 | A1 | 3/2015 | Nelms | |
| 2015/0238158 | A1* | 8/2015 | Zhou | G06T 7/12 |
| | | | | 382/131 |
| 2016/0129282 | A1 | 5/2016 | Yin et al. | |

OTHER PUBLICATIONS

Extended European Search Report issued in counterpart European Application No. 18170881.9 dated Jun. 29, 2018 (five (5) pages.
Notice of Allowance issued in counterpart U.S. Appl. No. 15/555,489 dated Sep. 25, 2019.
Supplemental Notice of Allowability issued in counterpart U.S. Appl. No. 14/893,055 dated Aug. 11, 2019.
Non-Final Office Action issued in counterpart U.S. Appl. No. 15/555,488 dated Mar. 22, 2019.
International Search Report and Written Opinion issued in PCT Application No. PCT/US2016/063204 dated Mar. 3, 2017, 7 pages.
Communication Pursuant to Rule 69 EPC issued in counterpart EP Application No. 18170881 dated Oct. 15, 2018 (two (2) pages).
Non-Final Office Action issued in counterpart U.S. Appl. No. 14/893,055 dated Jan. 11, 2019.
Decision of Rejection issued in counterpart Chinese Application No. 201480034786.7 dated Jul. 6, 2018 (five (5) pages).
Notification of Re-examination issued in counterpart Chinese application No. 201480034786.7 dated Jun. 28, 2019 (six (6) pages).
Communication under Rule 71(3) EPC issued in counterpart EP Application No. 18 170 881.9 dated May 21, 2019 (101 pages).
Notice of Allowance issued in counterpart U.S. Appl. No. 14/893,055 dated Jun. 7, 2019.
Final Office Action issued in counterpart U.S. Appl. No. 14/893,055 dated Sep. 10, 2018.
Non-Final Office Action issued in counterpart U.S. Appl. No. 15/555,489 dated Jul. 23, 2019.
Supplemental Notice of Allowability issued in counterpart U.S. Appl. No. 14/893,055 dated Aug. 7, 2019.

* cited by examiner

SYSTEMS AND METHODS FOR AUTOMATIC, CUSTOMIZED RADIATION TREATMENT PLAN GENERATION FOR CANCER

CROSS REFERENCE TO RELATED APPLICATIONS

This is a 371 national stage patent application, which claims priority to PCT International Patent Application No. PCT/US2016/063204, filed Nov. 21, 2016, and titled SYSTEMS AND METHODS FOR AUTOMATIC, CUSTOMIZED RADIATION TREATMENT PLAN GENERATION FOR CANCER, which claims the benefit of and priority to U.S. Provisional Patent Application No. 62/257,911, filed Nov. 20, 2015 and titled SYSTEMS AND METHODS FOR AUTOMATIC CUSTOMIZED RADIATION TREATMENT PLAN GENERATION FOR BREAST CANCER, and U.S. Provisional Patent Application No. 62/267,340, filed Dec. 15, 2015 and titled SYSTEMS AND METHODS FOR AUTOMATIC CUSTOMIZED RADIATION TREATMENT PLAN GENERATION FOR BREAST CANCER; the disclosures of which are incorporated herein by reference in their entireties.

STATEMENT AS TO FEDERALLY SPONSORED RESEARCH

This invention was made with the support of the United States government under Federal Grant No. R21CA161389 awarded by the National Institutes of Health (NIH). The government has certain rights in the invention.

TECHNICAL FIELD

The presently disclosed subject matter relates to radiation therapy. Particularly, the presently disclosed subject matter relates to systems and methods for automatic, customized radiation treatment plan generation for cancer.

BACKGROUND

Radiation therapy, or radiotherapy, is the medical use of ionizing radiation to control malignant cells. In intensity-modulated radiation therapy (IMRT), the intensity or segment of the radiation is modified in accordance with a treatment plan to deliver highly conformal radiation doses to the planning target volume (PTV) of malignant cells, while sparing the surrounding organs at risk (OARs) and other healthy tissues from radiation damage. By dividing the PTV and OAR volumes into individual volume elements (or "voxels"), the IMRT treatment plan can be characterized by a three-dimensional dose distribution that characterizes the magnitude of radiation at each of the voxels. Another effective, two-dimensional representation of the dose distribution is the dose volume histogram (DVH). Many clinical toxicity data and guidelines relating radiation damage to organs and radiation dose are expressed in DVH parameters (i.e., x1% volume, or x2 cc volume exceeding y1% or y2 Gy of dose).

A plan is Pareto optimal if it is impossible to further improve a certain dosimetric parameter without compromising the other parameters. Pareto optimal plans can include a set of plans that satisfy different planning criteria and objectives. The term intensity-modulated radiation therapy (IMRT) treatment plan (or simply "IMRT plan") hereby includes all forms of treatment plans that utilize radiation treatment processes in which radiation intensity can be delivered in a non-uniform manner, including but not limited to: intensity modulate radiation therapy (IMRT), volumetric modulated arc therapy (VMAT), treatment plans designed using TOMOTERPAY™, ACCURAY™, proton therapy, VIEWRAY™, VERO™, etc.

The development of an intensity-modulated radiation therapy (IMRT) treatment plan (or simply "IMRT planning") typically involves a complex optimization procedure by which the radiation beam angles and strengths are designed to achieve required dose of radiation for the planning target volume as prescribed, as well as limit the radiation delivered to neighboring normal tissues. While a portion of the IMRT planning process may be performed via computerized optimization algorithms, typically much of the process requires the input and expertise of a human planner. The computerized optimization algorithm calculates the current-state dose distributions/DVHs of each PTV and OAR, and compares those values to the input dose/DVH objectives. The differences of these two sets dose/DVH values are used to adjust the strength of each radiation beamlet based on pre-determined formula.

In particular, the human planner is typically responsible for manually adjusting input planning dose objectives (e.g., dose limits, dose volume histogram [DVH] limits, etc.) via a time-consuming, iterative trial-and-error process. The trial-and-error nature of the process is due to the fact that the planner does not know whether or not a set of given dose objectives will result in a plan that meets all physician-prescribed goals for sparing organs at risk (known as "sparing goals"), or when it does, whether tradeoffs between planning target volume (PTV) coverage and sparing of organs at risk (OARs) can be further improved.

Further compounding the process is the fact that physician-prescribed sparing goals are often adapted from clinical trial studies for general populations (e.g., the Radiation Therapy Oncology Group's (RTOG) sparing goals, the QUANTEC (Quantitative Analysis of Normal Tissue Effects in the Clinic) toxicity data, etc.) that ignore specific anatomical, geometric, and demographic information for individual patients, and often represent the upper limit of an organ's dose tolerance rather than an individual patient's lowest achievable dose in that organ. In summary, because of the lack of quantitative tools for linking variations in anatomy to variations in OAR sparing doses, planners must rely on personal experience and expertise when making adjustments for individual patients. Further, because of the lack of quantitative tools for providing trade-off options between various PTV coverage objectives and OAR sparing objective, physicians and planners must rely on personal experience and expertise when making treatment decisions for individual patients. It is noted that trade-off options may be discrete or continuous, meaning there may be two or more trade-off options made available to a user.

It is further noted that breast cancer accounts for 29% of new cancer diagnosis in 2015. According to American Cancer Society, 1 in 8 women is expected to develop breast cancer in their lifetime, ranking it the top prevalent cancer for women. Radiation treatment can reduce breast cancer recurrence by about 70% according to breastcancer.org, making it a critically essential part of cancer management and care.

The complexity and time commitment of manual breast treatment planning impedes the physician's ability to provide optimal care for their patients. Often physicians are not able to make sufficient adjustments or trade-offs between treating the cancer cells and protecting healthy tissue/organs, because the turnaround time is too long. In addition, the heavy reliance on planner's experience makes the plan quality highly varying across different practices. This makes it difficult to standardize the quality of care for all breast cancer, and leaving some patients receiving less-than-optimal care due to the lack of experience in some practices.

The prevalence of breast cancer, the need for high quality treatment plans, and the current suboptimal and non-standardized treatment planning process, call for improvement in the way that breast cancer radiation planning is generated.

BRIEF SUMMARY

Disclosed herein are systems and methods for automatic, customized radiation treatment plan generation for cancer. According to an aspect, a method includes receiving data indicating anatomy information of a patient and radiation beam characteristics of a radiation therapy system. Further, the method includes determining energy levels for application of radiation beams to the patient.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates. It should be stressed that, while the following description uses breast cancer treatment as an example, the same methods are applicable to all cancer types with similar characteristics. These other cancer types may include skin lesions with similar morphology.

The presently disclosed subject matter provides automated treatment planning systems and methods for breast radiation therapy that incorporates integrated physics-based and evidence-based models of breast treatment planning and generates high quality treatment plans. Such plans can be generated using a "one click" feature on a computing device. In accordance with embodiments, treatment planning techniques and experiences may be accumulated and collected via observing and analyzing human planning behavior, treatment planning system's response to manual adjustment. In accordance with embodiments, systems and techniques disclosed herein automate the planning process based on discovering, extracting, describing and integrating expert planner's thinking process and experiences from multiple comprehensive data sources.

In accordance with embodiments, systems disclosed herein for automated breast radiation therapy may use the following components: (1) intelligent beam energy selection; (2) multi-source evidence-driven fluence map generation (or equivalently, multiple MLC segments or sub-fields); and (3) patient- and physician-specific fluence fine-tuning. A system may work on each radiation field individually as well as the entire set of fields together to generate an optimal plan.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

As referred to herein, the term "computing device" should be broadly construed. It can include any type of device including hardware, software, firmware, the like, and combinations thereof. A computing device may include one or more processors and memory or other suitable non-transitory, computer readable storage medium having computer readable program code for implementing methods in accordance with embodiments of the present disclosure. A computing device may be, for example, retail equipment such as POS equipment. In another example, a computing device may be a server or other computer located within a retail environment and communicatively connected to other computing devices (e.g., POS equipment or computers) for managing accounting, purchase transactions, and other processes within the retail environment. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD). A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on smart phone, the examples may similarly be implemented on any suitable computing device, such as a computer. The system may be implemented in a cloud computing environment.

As referred to herein, the term "user interface" is generally a system by which users interact with a computing device. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

The present disclosed subject matter can provide radiation oncologists with practical and clinically accepted patient-specific optimal planning parameters predicted from models that formalize past experience and knowledge. Examples of this are provided in U.S. Patent Publication No. 2012/0014507 entitled "Automatic Generation of Patient-Specific Radiation Therapy Planning Parameters," the contents of which are hereby incorporated by reference in its entirety. Another aspect of the present disclosure provides for dose prediction models that are established by learning from databases of patient treatment plans generated by human expert planners, Pareto-optimal plans generated by the multi-objective optimizations or similar systems, and by learning from published radiation treatment guidelines, personal treatment planning knowledge, etc. A plan is Pareto optimal if it is impossible to further improve a certain dosimetric parameter without compromising the other parameters. Pareto optimal plans can include a set of plans that satisfy different planning criteria and objectives. The knowledge embedded in such plans/sources that are extracted into dose prediction models include, but are not limited to, (1) patient-specific anatomy features and its correlation to dose/DVHs in the OAR, based on his/her own unique tumor target and organ shape/positions relative to the tumor volume, and (2) clinical knowledge from the radiation oncologist's experience and expertise and planner's experience and expertise about beam configuration (e.g., energy, collimator size and orientations, special blocks, etc.), dose constraint settings (dose volume relations and weighing factors, etc.), and the like.

Figure 1:
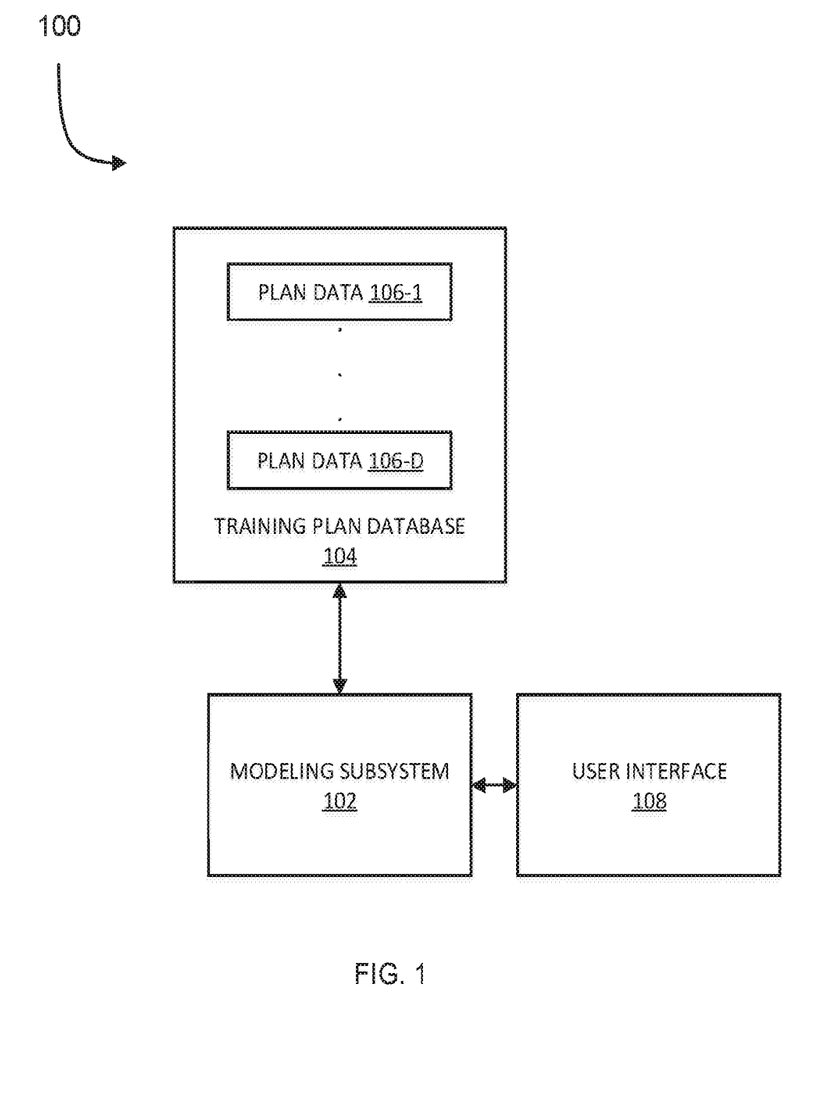
FIG. 1 illustrates a block diagram of an example system for radiation therapy planning in accordance with embodiments of the present disclosure.

FIG. 1 illustrates a block diagram of an example system 100 for radiation therapy planning in accordance with embodiments of the present disclosure. It is noted that the system 100 is described as being implemented by a single computing device in this example, although it should be appreciated that the system 100 may alternatively be implemented by one or more computing devices located locally together or remote from one another. The system 100 may be implemented by one or more processors and memory. For example, the system 100 may be suitably implemented hardware, software, firmware, or combinations thereof.

Referring to FIG. 1, the system 100 may include a modeling subsystem 102 and a training plan database 104 interconnected as shown. The modeling subsystem 102 is configured to read from and write to the training plan database 104, and other knowledge information such as guidelines, personal experiences, etc. The modeling subsystem 102 may generate a planning parameter for a new patient as described in more detail herein. Further, the modeling subsystem 102 is configured to store a representation of a predictive model, to train the predictive model, to generate a computer-executable program that applies the trained predictive model, and to execute tasks and functions described herein. Additional details of the modeling subsystem 102 is described herein.

The training plan database 104 is configured to provide persistent storage of data and efficient retrieval of the stored data. In an example, the database 104 may include records 106-1 through 106-D, where each record contains data associated with a training treatment plan that was formulated by an expert human planner for a patient. Example contents of the training plan database 104 are described in further detail herein.

Figure 2:
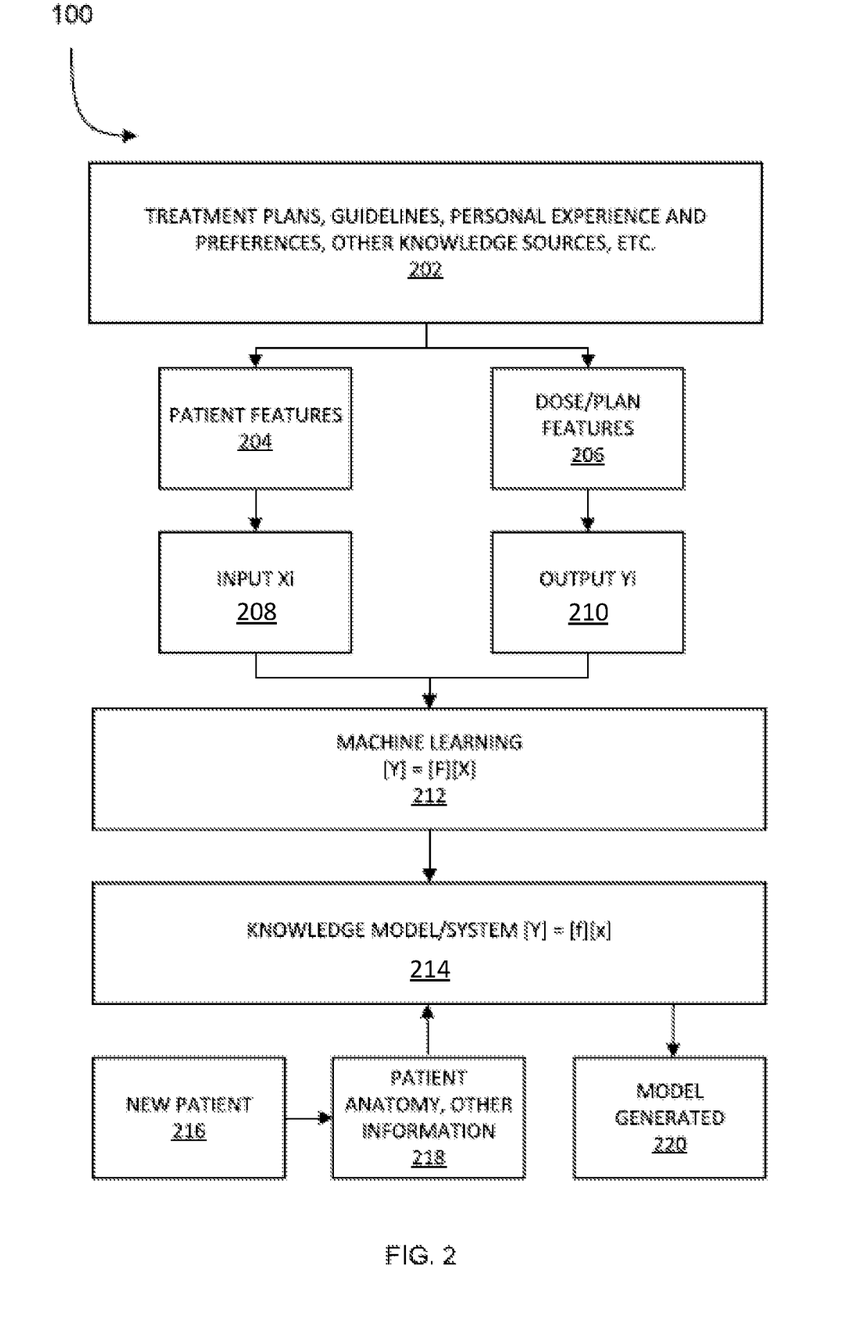
FIG. 2 illustrates a block diagram of another example system for radiation therapy planning in accordance with embodiments of the present disclosure.

FIG. 2 illustrates a block diagram of another example system 100 for radiation therapy planning in accordance with embodiments of the present disclosure. It is noted that the planning parameter-generation system is described as being implemented by a single computing device in this example, although it should be appreciated that the system may alternatively be implemented by one or more computing devices located locally together or remote from one another. The system 100 may be implemented by one or more processors and memory. For example, the system may be suitably implemented hardware, software, firmware, or combinations thereof. The system may provide automated treatment planning for breast radiation therapy that incorporates integrated physics-based and evidence-based models of breast treatment planning and that generates high quality treatment plans. It is noted that the example systems disclosed herein are described as being used for breast radiation therapy; however, it should be appreciated that the systems and their methods may also suitably be applied to other types of radiation therapies.

Referring to FIG. 2, the system includes providing 202 treatment plans, guidelines, personal experience and preferences, other knowledge sources, etc. This information may be provided to a database. In an example, this information may all be related to breast cancer treatment. In an example, treatment planning techniques and experiences may be accumulated and collected via observing and analyzing human planning behavior, and treatment planning system's response to manual adjustment. Patient features 204 and dose/plan features 206 may be placed into input $X_i$ 208 and output $Y_i$ 210, respectively, which may be placed into machine learning block 212. These components may be involved in the training of the model. Subsequent components relate to application of the model in a knowledge model/system 214.

Subsequently, new patient information 216 may be input. This information (e.g., patient anatomy, other information and conditions) may be characterized as patient feature $X_{new}$. The system 100 may use this new patient information to generate and output model generated treatment plan parameters 220 as $Y_{new}$ (beam energy, fluence maps, DVHs, other dose parameters). The system 100 may generate the model based on discovering, extracting, describing and integrating expert planner's thinking process and experiences from multiple comprehensive data sources. In accordance with embodiments, the system 100 may include the following functions: (1) intelligent beam energy selection; (2) multi-source evidence-driven fluence map generation (or equivalently, multiple MLC segments or sub-fields); and (3) patient- and physician-specific fluence fine-tuning. The system 100 may work on each radiation field individually as well as the entire set of fields together to generate an optimal plan or model.

In accordance with embodiments, systems and methods disclosed herein can construct an optimal energy selection tool and extract factors influencing a radiation therapy decision. The information used by the system for the energy selection algorithm is a patient's anatomy and/or a simplified representation—digitally reconstructed radiographs (DRRs) projected along the beam direction, for example. Based upon the intensity histogram of the DRRs and the anatomy characteristics, the algorithm identifies key parameters that best distinguishes different energy selections, and uses these parameters to make energy recommendations in the energy selection tool. In a scenario in which the system 100 determines to use mixed energy, the ratio splitting contributions from low and high energy components (e.g., 6× and 15×) can either be automatically suggested by the energy selection tool or supplied by a user.

In some clinical treatment planning scenarios, a planner manually adjusts fluence intensities or MLC segments in a forward-planning process, i.e. the planner uses trial-and-adjust strategies without knowing what uniformity can be achieved. This process can suffer from very low efficiency. In addition, after each adjustment on local fluence intensities, often involving only a few cm² area in the two-dimensional (2D) fluence map, a full three-dimensional (3D) dose calculation has to be performed for the planner to see the result of his or her last adjustment, and then decide if and how to perform further adjustment. Because each calculation takes about 30 seconds to 1 minute, the planning process is further slowed down by this manual iterative process. In another planning format, the planner defines the entire breast as a planning-target-volume (PTV) and other organs-at-risk (OAR) such as lung and heart, then use the inverse planning algorithm to generate the fluence map or MLC segments. In this process, the inverse algorithm tries to minimize a predetermined objective function, consisting of different goals for covering PTV and sparing OAR, via adjusting the fluence maps.

In accordance with embodiments, a system as disclosed herein may determine patient-specific fluence map/MLC segments in a one-stop fashion without the need for target delineation or inverse optimization. The system may characterize the physical properties of beamlets interacting with the patient and may determine the key parameters and processes to adjust the intensity of the fluence map/MLC segments based on the location of the influenced voxel in the patient with the goal to provide dose coverage that is as uniform as possible for the entire breast. It is noted that in at least some embodiments, the modeling is not case specific, planning technique specific, or IMRT/VMAT specific. The modeling disclosed herein may only be dependent on beam characteristics. This distinction can mean that the model need only be built once for a particular linear accelerator, and can be used in any institution, by any suitable planning/prescribing techniques, and for any patient population. This makes systems disclosed herein very easy to use and very versatile.

Fluence map/MLC segments generated as described herein can provide a suitable baseline that balances breast tissue coverage and uniformity/hotspot. However, physicians may have their own considerations based on patient-specific information for target coverage or hotspot volume control. This third step can offer the physician the opportunity to interactively fine-tune the 3D dose distribution. This step can start with finding reference points in the breast tissue, followed by reference point centrality and fluence fine-tuning.

Reference points may be first identified automatically based on beam geometric configuration and the position of the isocenter in the patient body. The locations of the reference points may subsequently be fine-tuned using anatomical information of the current patient. This patient-specific fine-tuning can allow the algorithm to account for clinical considerations that are not covered in the baseline model yet still important to tailor the fluence map for a particular patient, such as extra skill dose buildup or heart avoidance.

In a subsequent or final stage, the algorithm can make further fine adjustments on the fluence maps/MLC segments based on physician's requirements. The algorithm can, for example, accommodate the following requirements:
  Higher/lower skin dose;
  Higher/lower chest wall coverage;
  Inhomogeneity correction on/off during dose calculation; and
  Other OAR avoidance.

This automated treatment planning platform can seamlessly interface with treatment planning systems to allow users to very conveniently incorporate this system into a current clinical environment without the need to make changes to their current treatment planning systems.

The high efficiency and automation of the plan generation process can enable physicians to focus on tweaking and customizing treatment plans to best fit each patient's unique situation. The integrated plan customization module can give physicians the freedom to make trade-off decisions on the fly and immediately see the resulting radiation dose superimposed on a patient's anatomy. The portability of this anatomy-to-fluence/MLC segments technique can allow easy adoption of this automated planning platform in clinical and research environments with minimal configuration and commissioning effort.

Figure 3A:
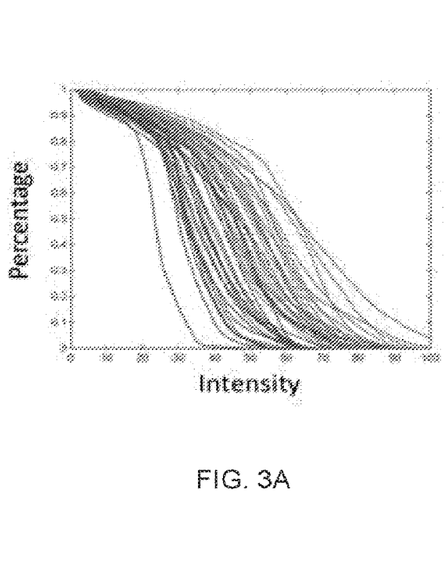
FIG. 3A illustrates a graph showing a DRR intensity histogram for single energy cases and mix energy cases.
Figure 3B:
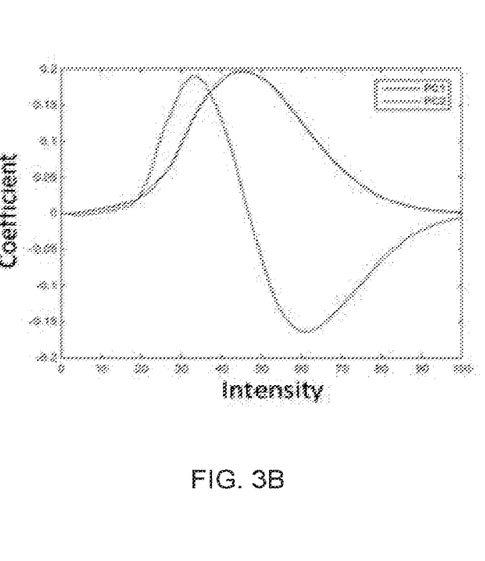
FIG. 3B illustrates a graph showing PC coefficient for PC1 and PC2.
Figure 3C:
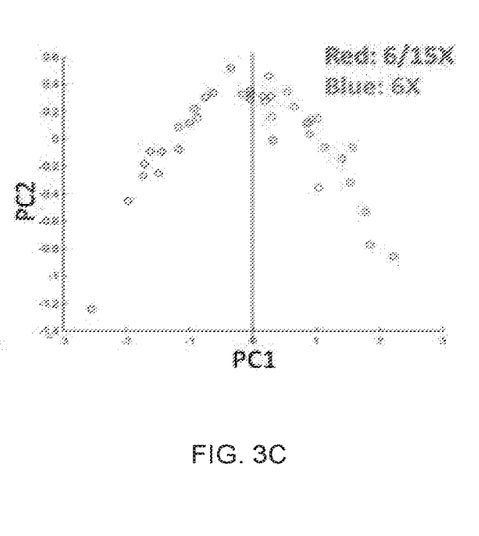
FIG. 3C illustrates a graph showing PC1 and PC2 score for single energy cases and mixed energy cases.

In accordance with embodiments, a system, such as system 100 shown in FIGS. 1 and 2, may implement an intelligent beam energy selection algorithm. In this function, the system may use sample anatomy and dose distributions to determine parameters for energy selection. The algorithm may use both the patient 3D anatomy and the digital reconstructed radiograph (DRR) as a representation for patient anatomy projected to each beam's direction. For example, FIG. 3A illustrates a graph showing a DRR intensity histogram for single energy cases and mix energy cases. FIG. 3B illustrates a graph showing PC coefficient for PC1 and PC2. FIG. 3C illustrates a graph showing PC1 and PC2 score for single energy cases and mixed energy cases. Principal component analysis (PCA) may be performed and the first two component score may be used to represent each case (FIG. 3C).

Figure 4A:
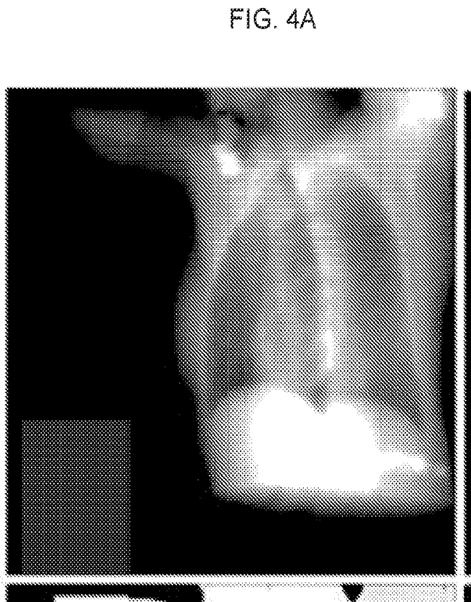
FIGS. 4A-4D illustrate an example feature map included in RF: DRR, penetration depth, inverse square factor, and penetration depth in tissue excluding lung.
Figure 4B:
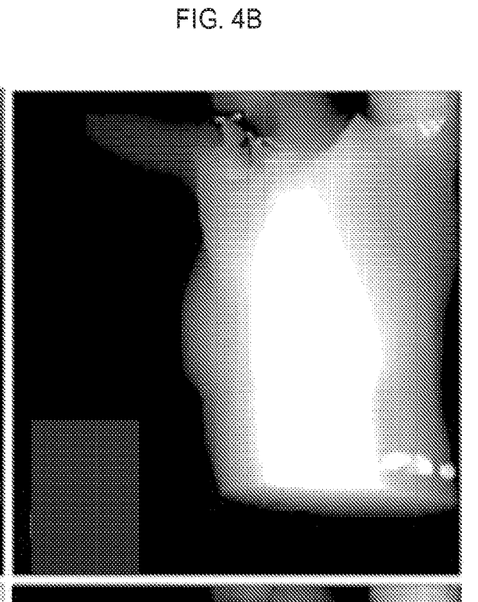
Figure 4C:
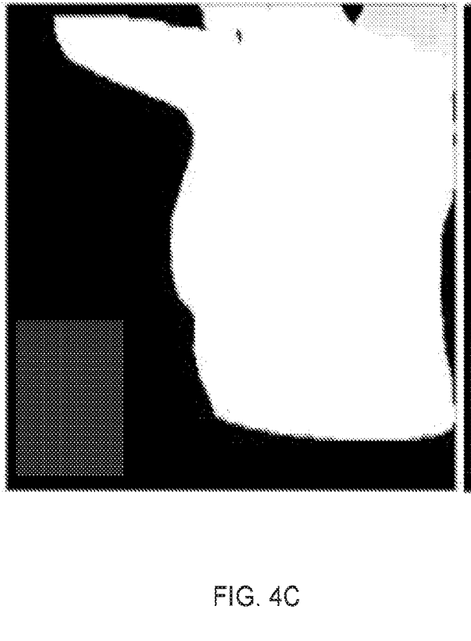
Figure 4D:
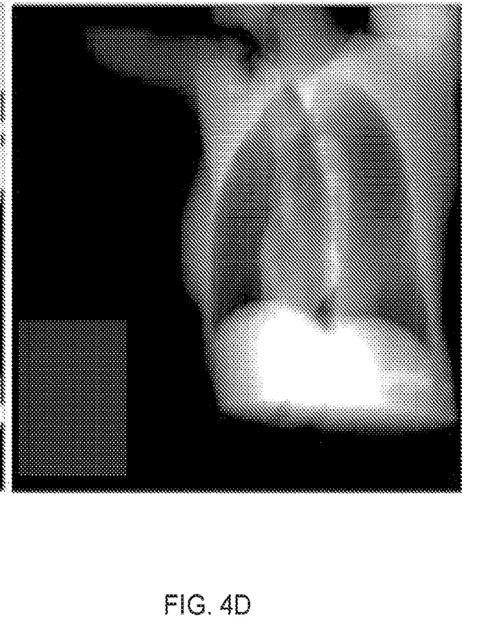

In accordance with embodiments, a system, such as system 100 shown in FIGS. 1 and 2, may implement an anatomy-driven fluence map generation algorithm. In this function, at least some of the key factors may be used as fluence/intensity predictors. Key features used in this function are depicted in FIGS. 4A-4D, which illustrate an example feature map included in machine learning models such as random forest (RF): DRR (FIG. 4A); penetration depth (FIG. 4B); inverse square factor (FIG. 4C); and penetration depth in tissue excluding lung (FIG. 4D).

Figure 5A:
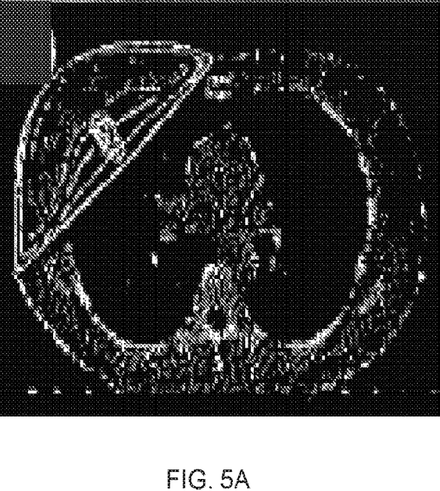
FIG. 5A is an image of an example reference points located on the iso-plane, reference points in the tissue and the lung are shown.
Figure 5B:
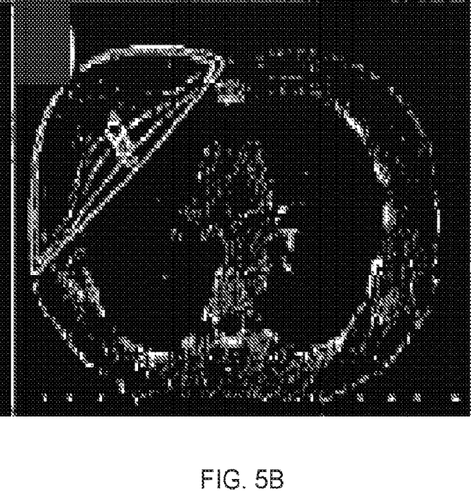
FIG. 5B is an image showing reference points in the breast tissue after centrality correction.
Figure 5C:
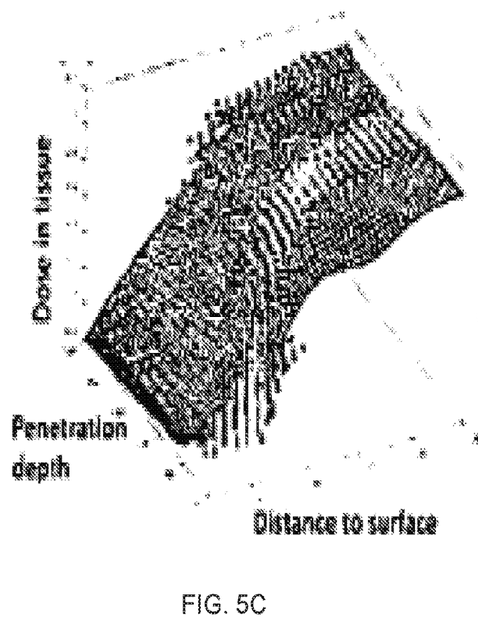
FIG. 5C is a graph showing example dose in the tissue near skin.
Figure 5D:
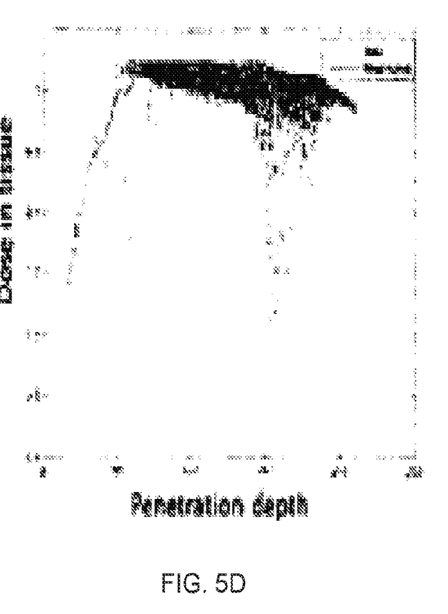
FIG. 5D is a graph showing example dose in the tissue near chest wall.

In accordance with embodiments, a system, such as system 100 shown in FIGS. 1 and 2, may implement fluence fine-tuning including reference point selection and centrality correction. For example, the system may identify reference points on the iso-plane in the irradiate volume (shown in FIG. 5A for example). FIG. 5A is an image of an example reference points located on the iso-plane, reference points in the tissue and the lung are shown. Centrality correction may subsequently be performed to balance the penetration tissue from either side for reference points in the breast tissue (shown in FIG. 5B). Baseline dosimetric parameters can be tuned towards specific coverage requirement or hotspot control. FIG. 5B is an image showing reference points in the breast tissue after centrality correction. The baseline parameters for reference points near skin and near chest wall are shown in FIGS. 5C and 5D. FIG. 5C is a graph showing example dose in the tissue near skin. FIG. 5D is a graph showing example dose in the tissue near chest wall.

Figure 6:
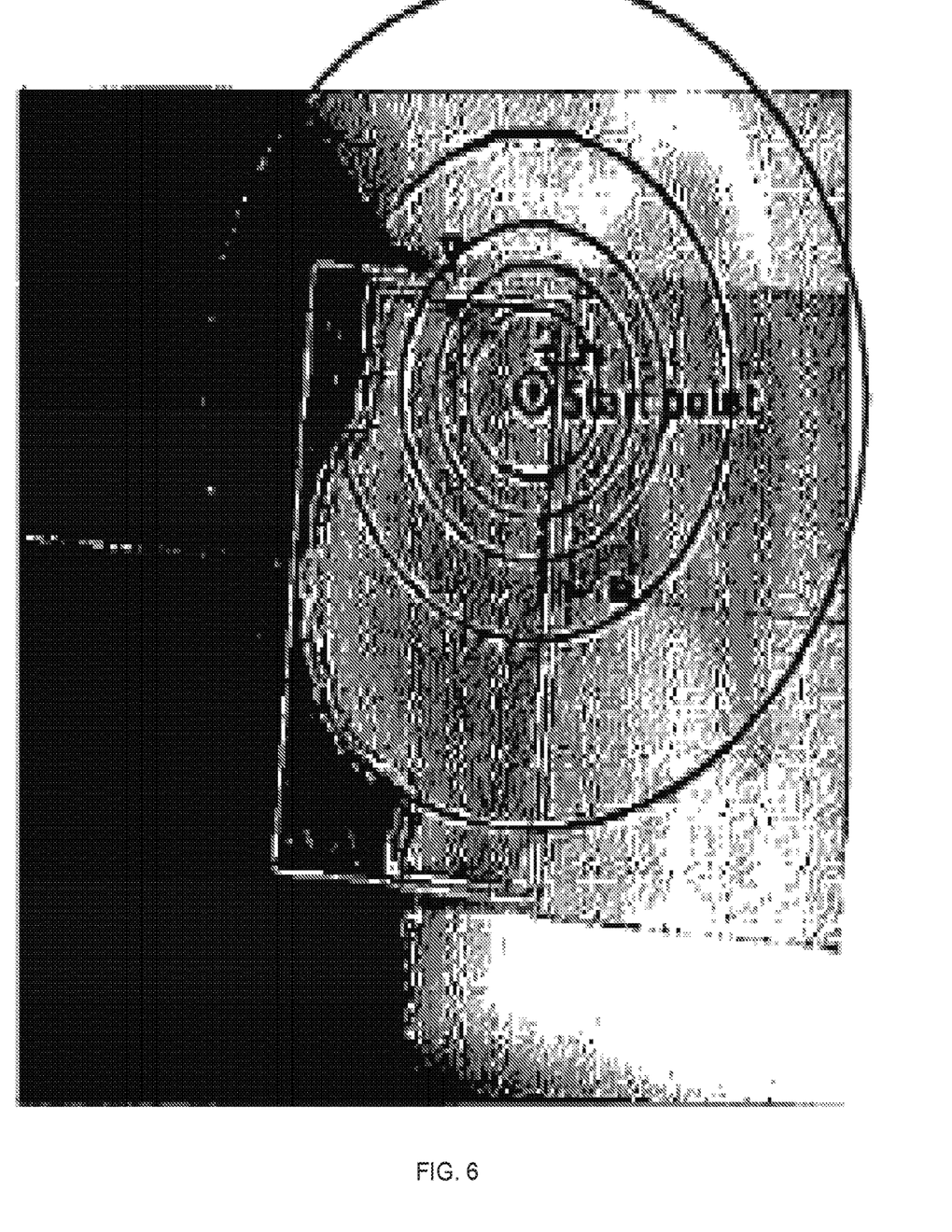
FIG. 6 illustrates a fluence tuning path in the beam-eye-view.

In accordance with embodiments, a system, such as system 100 shown in FIGS. 1 and 2, may implement fluence fine-tuning including physician- and patient-specific adjustment. For example, the fluence fine-tuning starts from the beamlet that connects the radiation source (shown as the start point in FIG. 6). The beamlet is tuned radially from the start point to the peripheral zones. Particularly, FIG. 6 illustrates a fluence tuning path in the beam-eye-view. The fluence tuning starts from the center (start point) and spreads radially. The tuned fluence may satisfy the following condition:

$$f = \operatorname{argmin} \sum_i (D_i(f) - D_{i,model})$$

where i is reference point, $D_i(f)$ is the dose at reference point i after fluence tuning, $D_{i,model}$ is tunable dose parameter shown in FIGS. 5C and 5D.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flow chart illustrations and/or block diagrams of methods, apparatus (systems), and computer program products according to embodiments of the subject matter. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow chart and/or block diagram block or blocks.

The flow chart and block diagrams in the Figures illustrate the architecture, functionality, and operation of possible implementations of systems, methods, and computer program products according to various embodiments of the present subject matter. In this regard, each block in the flow chart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts or carry out combinations of special purpose hardware and computer instructions.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method comprising:
    at a processor and memory:
        receiving anatomy information of a patient;
        receiving radiation beam characteristics of a radiation therapy system; and
        generating a fluence map for the patient without an optimization step, based on the anatomy information and the radiation beam characteristics.

2. The method of claim 1, wherein receiving anatomy information comprises receiving data indicating breast anatomy.

3. The method of claim 1, wherein receiving anatomy information comprises receiving beam-anatomy interaction features projected along a direction of one or more of the radiation beams.

4. The method of claim 1, further comprising determining energy levels for application of radiation beams to the patient, wherein determining energy levels comprises selecting beam energy and analyzing a ratio of different energy components in dual energy breast treatment.

5. The method of claim 1, further comprising determining energy levels for application of radiation beams to the patient, wherein determining energy levels comprises:
    analyzing physical properties of a radiation beam interacting with a patient; and
    estimating associated radiation intensity and generating optimal dose distribution with a treatment volume based on the physical and anatomical properties.

6. The method of claim 1, further comprising determining wherein generating the fluence map for the patient comprises:
    characterizing one or more MLC segments as the MLC segments interact with patient anatomy; and
    adjusting the intensity of the MLC segments using a predictive model.

7. The method of claim 6, further comprising generating a predictive model, comprising:
    collecting a plurality of high quality prior cases of treatment planning of similar nature;
    extracting key patient features; and
    training the predictive model for generating optimal fluence maps.

8. The method of claim 7, wherein the key patient features comprise one or more of: DRR; penetration depth; inverse square factor; and penetration depth in tissue.

9. The method of claim 7, wherein the predictive model comprises machine learning algorithms.

10. The method of claim 7, further comprising key feature extraction methods that do not require delineation between target organs and organs at risk.

11. The method of claim 1, further comprising extending radiation fluence outside of skin of the patient.

12. The method of claim 1, further comprising:
    identifying reference points in the patient anatomy; and
    monitoring and controlling dose distribution within an irradiated volume of the patient by adjusting associated radiation beam intensity based on the reference points.

13. The method of claim 1, further comprising presenting the determined fluence map via a user interface.

14. A system comprising:
at least one processor and memory configured to:
receive anatomy information of a patient;
receive radiation beam characteristics of a radiation therapy system; and
generate a fluence map for the patient without an optimization step, based on the anatomy information and the radiation beam characteristics.

15. The system of claim 14, wherein the anatomy information comprises data indicating breast anatomy.

16. The system of claim 14, wherein the anatomy information comprises beam-anatomy interaction features projected along a direction of one or more of the radiation beams.

17. The system of claim 14, wherein the at least one processor and memory are configured to determine energy levels for application of radiation beams to the patient by selecting beam energy and analyzing a ratio of different energy components in dual energy breast treatment.

18. The system of claim 14, wherein the at least one processor and memory are configured to determine energy levels for application of radiation beams to the patient by:
analyzing physical properties of a radiation beam interacting with a patient; and
estimating associated radiation intensity and generating optimal dose distribution with a treatment volume based on the physical and anatomical properties.

19. The system of claim 14, wherein the at least one processor and memory are configured to generate the fluence map by:
characterizing one or more MLC segments as the MLC segments interact with patient anatomy; and
adjusting the intensity of the MLC segments using a predictive model.

20. The system of claim 19, wherein the at least one processor and memory are configured to generate a predictive model by:
collecting a plurality of high quality prior cases of treatment planning of similar nature;
extracting key patient features; and
training the predictive model for generating optimal fluence maps.

21. The system of claim 20, wherein the key patient features comprise one or more of: DRR; penetration depth; inverse square factor; and penetration depth in tissue.

22. The system of claim 20, wherein the predictive model comprises machine learning algorithms.

23. The system of claim 20, further comprising key feature extraction methods that do not require delineation between target organs and organs at risk.

24. The system of claim 14, wherein the at least one processor and memory are configured to extend radiation fluence outside of skin of the patient.

25. The system of claim 14, wherein the at least one processor and memory are configured to:
identify reference points in the patient anatomy; and
monitor and controlling dose distribution within an irradiated volume of the patient by adjusting associated radiation beam intensity based on the reference points.

26. The system of claim 14, wherein the at least one processor and memory are configured to present the determined fluence map via a user interface.

27. A computer program product comprising a computer readable storage medium having program instructions embodied therewith, the program instructions by a computing device to cause the computing device to:
receive, by the computing device, anatomy information of a patient and radiation beam characteristics of a radiation therapy system; and
generate a fluence map for the patient without an optimization step, based on the anatomy information and the radiation beam characteristics.

* * * * *